United States Patent [19]

Shouldice et al.

[11] Patent Number: 4,857,181
[45] Date of Patent: Aug. 15, 1989

[54] CONTROL OF CLEANING OF DIALYSATE PREPARATION APPARATUS

[75] Inventors: David R. Shouldice, Lakewood; Dennis M. Treu, Morrison; Daniel A. Powell, Littleton; Thomas Cernich, Denver, all of Colo.

[73] Assignee: Cobe Laboratories, Inc., Lakewood, Colo.

[21] Appl. No.: 925,822

[22] Filed: Oct. 30, 1986

[51] Int. Cl.⁴ ............................................. B01D 13/00
[52] U.S. Cl. ................................. 210/87; 134/166 C; 134/171; 210/321.69
[58] Field of Search ...................... 210/87, 321.3, 96.2, 210/140, 321.69; 134/57 R, 166 C, 171

[56] References Cited

U.S. PATENT DOCUMENTS

| | | | |
|---|---|---|---|
| 3,753,493 | 8/1973 | Mellor | 210/140 |
| 3,871,913 | 3/1975 | Shaldon | 210/321.69 |
| 4,158,034 | 6/1979 | Riede et al. | 210/321.69 |
| 4,166,031 | 8/1979 | Hardy | 210/321.69 |
| 4,209,402 | 6/1980 | Gentles | 210/140 |
| 4,361,485 | 11/1982 | Boonstra | 210/321.69 |
| 4,371,385 | 2/1983 | Johnson | 210/321.2 X |
| 4,411,866 | 10/1983 | Kanno | 210/321.69 |
| 4,444,597 | 4/1984 | Gortz et al. | 210/321.3 X |

Primary Examiner—W. Gary Jones

[57] ABSTRACT

Dialysate preparation apparatus having a main flow line having one end for connection to a source of water and another end for providing dialysate to a dialyzer, a concentrate flow line having one end connected to a junction on the main flow line and another end with a connector for alternatively connecting the concentrate line to a source of dialysate concentrate or a source of cleaning fluid, a source of dialysate connectable to the connector, a source of cleaning fluid having a cleaning fluid flow line with an end that is connectable to the connector, a flow sensing switch on the cleaning fluid flow line, and a controller connected to receive a signal from the switch to verify that the apparatus is in a cleaning mode when the switch indicates fluid flowing in the flow line. Also disclosed is a controller providing an initial backflush prior to pumping cleaning fluid into the apparatus in order to provide a water interface between the dialysate and the incoming cleaning fluid.

8 Claims, 1 Drawing Sheet

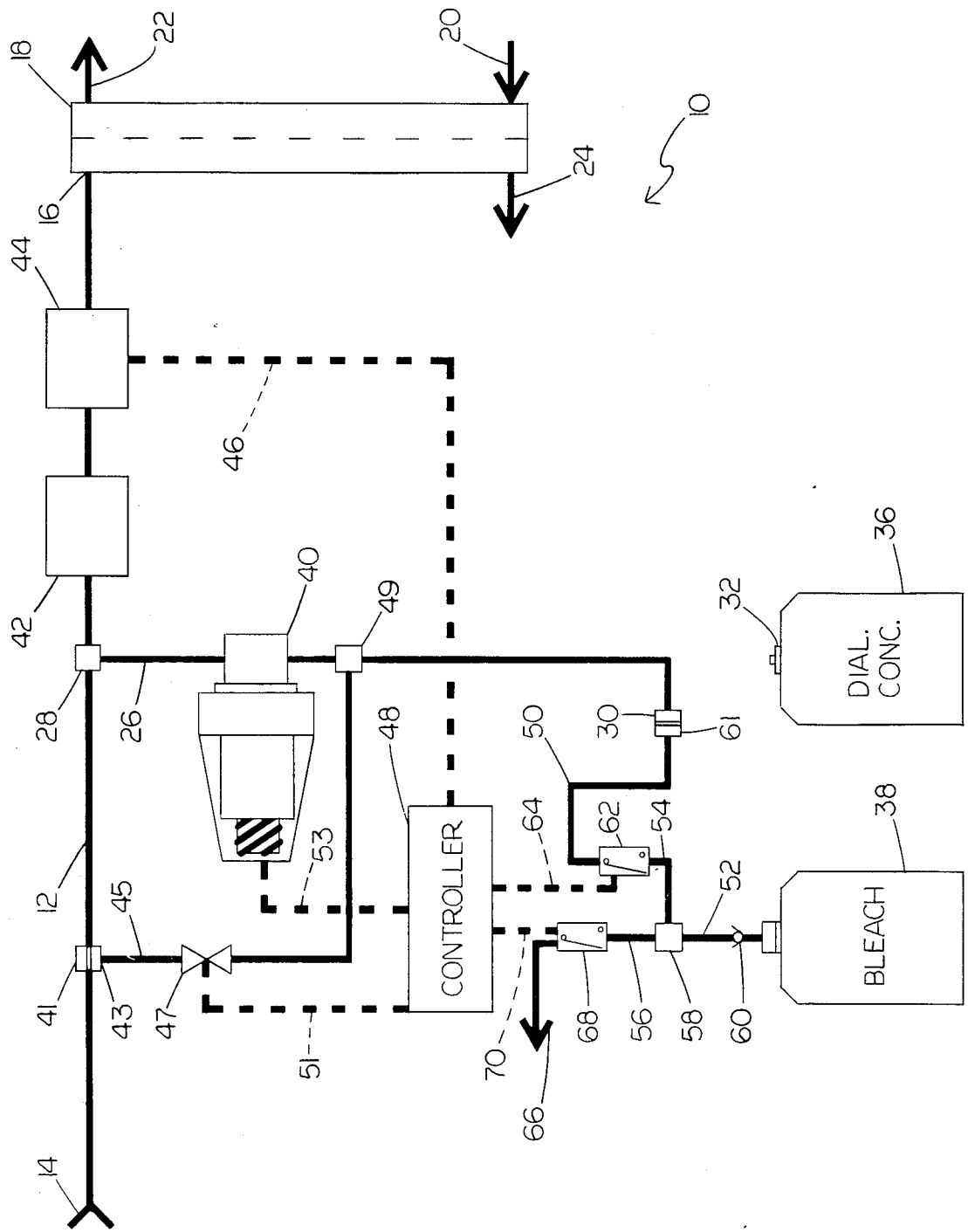

4,857,181

CONTROL OF CLEANING OF DIALYSATE PREPARATION APPARATUS

FIELD OF THE INVENTION

The invention relates to dialysate preparation apparatus for mixing dialysate concentrate with water.

BACKGROUND OF THE INVENTION

In dialysate preparation apparatus of the type shown in Johnson U.S. Pat. No. 4,371,385 (which is hereby incorporated by reference), water is heated, deaerated, and mixed with dialysate concentrate to continuously provide dialysate supplied to a dialyzer used with a patient. In such apparatus, dialysate concentrate is typically pumped to a junction on a main flow line for mixing with water. A downstream conductivity cell is used to sense the conductivity of the mixed solution passing through it (which conductivity is related to the concentration of elements of the dialysate in the water), and this is used in a control loop to control the pump for dialysate concentrate. When such apparatus is disinfected and cleaned, between uses with different patients, bleach or disinfectant is flushed through the hydraulic circuitry of the dialysate preparation apparatus. "Cleaning fluid" herein means bleach or disinfectant or other chemicals which are flushed through the hydraulic circuitry.

SUMMARY OF THE INVENTION

In one aspect the invention features in general dialysate preparation apparatus having a concentrate flow line with an end connected to a junction on a main line and another end that is alternatively connectable to a source of dialysate concentrate or a cleaning fluid flow line that has a flow-sensing switch on it so that a controller for the apparatus can verify that the apparatus is in the cleaning mode when the switch indicates fluid flowing in the cleaning fluid line.

In another aspect the invention features in general dialysate preparation apparatus including a concentrate flow line having one end connected to a junction on a main flow line and another end alternately connectable to a source of dialysate concentrate or a source of cleaning fluid; a drain is connected to the concentrate line, and a controller initially flushes the concentrate line to the drain in order to remove concentrate from the concentrate line and to fill it with water prior to pumping cleaning fluid through the concentrate line. This provides a water interface between the dialysate and the incoming cleaning fluid, preventing precipitates from forming. In preferred embodiments the cleaning fluid line has three segments connected at a junction, the first segment being connected between the source of cleaning fluid and the junction, the second segment being connected between the junction and the connector to the concentrate line, and the third segment being connected between the junction and the drain.

Other features and advantages of the invention will be apparent from the following description of a preferred embodiment thereof and from the claims.

DESCRIPTION OF THE PREFERRED EMBODIMENT

The preferred embodiment will now be described.

DRAWING

The drawing is diagrammatic representation of dialysate preparation apparatus according to the invention.

STRUCTURE

Referring to the drawing, there is shown dialysate preparation apparatus 10, including main flow line 12 having end 14 for connection to a source of water and another end connected to inlet 16 of dialyzer 18, having blood inlet 20 and blood outlet 22 connected to a patient and dialysate outlet 24. Concentrate line 26 is connected at one end to junction 28 on main flow line 12 and at the other end has connector 30 for connection to fitting 32 on dialysate concentrate (acetate) jug 36 or fitting 61 connected through cleaning fluid line 50 to bleach jug 38.

On concentrate flow line 26 is volumetric diaphragm pump 40 that has a fixed discharge volume per stroke. Downstream of junction 28 on main flow line 12 are mixing chamber 42 and conductivity cell 44. Pump 40 is controlled by a feedback loop based on the conductivity sensed by sensor 44, which loop is indicated by dashed line 46 to controller 48 and dashed line 53 to pump 40 in the drawing. Pump 40 is also connected to electronic controller 48 to provide controller 48 with information indicating the stroke rate (stroke/time) of pump 40. Controller 48 includes a comparator to compare the stroke rate from pump 40 with a limit indicating desired operating stroke rate range.

Connected to rinse port 41 on main flow 12 upstream of junction 28 is removable fitting 43, connected via bypass flow line 45, having valve 47, to junction 49 on concentrate line 26. Valve 47 is controlled by signals over line 51 from controller 48 to be open or closed.

Cleaning fluid line 50 has three segments 52, 54, and 56, all connected to junction 58. First segment 42 is connected between the fitting on top of bleach jug 38 and junction 58, and has check valve 60 permitting unidirectional flow from jug 38 to junction 58. Second segment 54 is connected between junction 58 and fitting 61 connected to connector 30. On segment 54 is flow sensing switch 62 providing a signal over line 64 to controller 48 indicating flow through it toward concentrate line 26. Third segment 56 is connected between junction 58 and drain 66 and has flow sensing switch 68 providing a signal over line 70 to controller 48 indicating flow through it toward drain 66.

Apparatus 10 also includes a heat exchanger, a combined heater/deaerator, balance chambers (to balance the flow into the dialyzer with that coming out of the dialyzer to control ultrafiltration) and further conductivity cells and a pH sensor, all not shown. It also has a further concentrate flow line connected to main flow line 12 upstream of juncton 28 to permit separate pumping of bicarbonate and acid solutions; part of the further concentrate line includes part of bypass flow line 45.

OPERATION

In operation water is provided to flow line 12 at end 14, and dialysate concentrate is pumped by pump 40 to junction 28, in which there is initial mixing of water with the concentrate. Further mixing occurs in mixing chamber 42, which has a vent connected to a vacuum pump (not shown) to remove any gas volatilized from the solution. From mixing chamber 42, the mixed dialysate concentrate/water solution passes through conductivity cell 44, and from there it flows to the dialysate side of the membrane in dialyzer 18. The conductivity sensed by sensor 44 is fed back and used to control pump 40 to achieve a conductivity associated with desired dialysate concentration. The stroke rate of pump 40 is automatically monitored by controller 48, which continuously compares it with a range of desired operating stroke rates for the particular concentrate. The continuous monitoring of the stroke rate by controller 48 prevents use of an improper chemical that could be proportioned to a conductivity setpoint and cause patient harm.

Between use with different patients, the hydraulic circuitry is rinsed with water and flushed with cleaning fluids, some of which may remain in the circuitry for a period of time. E.g., bleach in jug 38, shown in drawing, is flushed through the system using pump 40 after connector 30 has been connected to fitting 61 on segment 54.

When beginning the cleaning mode, fitting 43 is connected to rinse port 41, and valve 47 is initially opened to provide a backflush in which water flows through concentrate line 26, segment 54, and segment 56 to drain 66. During this backflush, flow sensing switch 68 verifies that fitting 61 has, in fact, been connected to connector by the operator. The backflush rinse lasts two minutes so that a water interface is created between the dialysate and the incoming bleach from jug 38. Bleach is pumped from jug 38 through concentrate line 26 and the remainder of the system. When liquid is flowing through flow-sensing switch 62 to concentrate line 26, a signal indicating this is provided to controller 48 to verify that the apparatus is in the cleaning mode. If not, the machine will cause an alarm to sound, and this will require the machine to be turned off, and a manditory forced rinse of the machine will be initiated on power-up.

Other embodiments of the invention are within the scope of the following claims.

What is claimed is:

1. Dialysate preparation apparatus comprising
   a main flow line having one end connected to a source of water and another end for connecting to a dialyzer for providing dialysate to said dialyzer,
   a concentrate flow line having one end connected to a junction on said main flow line and another end with a connector for alternatively connecting said concentrate line to a source of dialysate concentrate or a source of cleaning fluid,
   a source of dialysate connectable to said connector,
   a source of cleaning fluid including a cleaning fluid flow line with an end that is connectable to said connector,
   a flow sensing switch means on said cleaning fluid flow line for providing a verification signal indicating fluid flowing in said flow line, and
   a controller means connected to receive said verification signal from said flow sensing switch for verifying that said apparatus is in a cleaning mode when said flow sensing switch indicates fluid flowing in said cleaning fluid flow line.

2. Dialysate preparation apparatus comprising
   a main flow line having one end connected to a source of water and another end for connecting to a dialyzer for providing dialysate to said dialyzer,
   a concentrate flow line having one end connected to a junction on said main flow line and another end with a connector for alternatively connecting said concentrate line to a source of dialysate concentrate or a source of cleaning fluid,
   a pump on said concentrate line,
   water supply means to provide water under pressure to said concentrate line between said pump and said connector,
   a cleaning fluid flow line having an end connectable to said connector and a first segment connected to a source of cleaning fluid and permitting unidirectional flow through it from said source of cleaning fluid,
   a drain means connected to said cleaning fluid line for permitting draining of liquid in said concentrate line,
   a controller means for controlling said water supply means during a cleaning mode to initially backflush water through said concentrate line and said cleaning fluid line to said drain means in order to replace said concentrate with water, thereby providing a water interface between said concentrate and said cleaning fluid, said controller means thereafter controlling said pump to pump cleaning fluid from said source through said concentrate line.

3. The apparatus of claim 2 wherein said cleaning fluid line has second and third segments and a junction connected to said first, second, and third segments, said first segment being connected between said source of cleaning fluid and said junction connected to said first, second, and third segments, said second segment being connected between said junction connected between said first, second, and third segments and said end of said cleaning fluid line, and said third segment being connected between said junction connected between said first, second, and third segments and said drain means.

4. The apparatus of claim 3 wherein said cleaning fluid line includes a first flow switch electrically connected to said controller to verify that said flush of water has occurred.

5. The apparatus of claim 4 further comprising a second flow switch to sense when fluid is flowing from said source of cleaning fluid to said connector, said second switch being electrically connected to said controller, said controller including means to verify that the apparatus is in a cleaning mode when said switch indicates fluid flowing in said cleaning fluid line.

6. The apparatus of claim 2 in which said water supply means comprises a bypass flow line connected from said main flow line upstream of said junction to said concentrate line between said pump and said connector.

7. The apparatus of claim 6 further comprising a valve on said bypass flow line.

8. The apparatus of claim 7 wherein said bypass flow line is removably connectable to said main flow line.

* * * * *